United States Patent [19]

Allen, Jr. et al.

[11] Patent Number: 5,776,491
[45] Date of Patent: *Jul. 7, 1998

[54] RAPIDLY DISSOLVING DOSAGE FORM

[75] Inventors: Loyd V. Allen, Jr., Edmond; Bingnan Wang, Oklahoma City, both of Okla.; John Desmond Davies, Grosse Pointe Farms, Mich.

[73] Assignees: The Board of Regents of the University of Oklahoma, Norman, Okla.; Janssen Pharmaceutica, Inc., Ann Arbor, Mich.

[ * ] Notice: The term of this patent shall not extend beyond the expiration date of Pat. No. 5,766,630.

[21] Appl. No.: 487,268

[22] Filed: Jun. 7, 1995

Related U.S. Application Data

[63] Continuation of Ser. No. 191,237, Feb. 3, 1994.
[51] Int. Cl.⁶ .............. A61K 9/20; A61K 9/28; A61K 9/46
[52] U.S. Cl. .............. 424/465; 424/466; 424/474
[58] Field of Search .............. 424/486, 465, 424/466, 474, 482, 489, 488; 514/960

[56] References Cited

U.S. PATENT DOCUMENTS

| | | | |
|---|---|---|---|
| 4,013,784 | 3/1977 | Speiser | 424/19 |
| 4,572,832 | 2/1986 | Kigasawa et al. | 424/19 |
| 5,082,667 | 1/1992 | Van Scoik | 424/469 |
| 5,178,878 | 1/1993 | Wehling et al. | 424/466 |
| 5,215,756 | 6/1993 | Gole et al. | 424/484 |

FOREIGN PATENT DOCUMENTS

| | | |
|---|---|---|
| 2111423 | 7/1983 | United Kingdom . |
| 9310762 | 6/1993 | WIPO . |
| 9414422 | 7/1994 | WIPO . |

*Primary Examiner*—Edward J. Webman
*Attorney, Agent, or Firm*—Dunlap & Codding, P.C.

[57] ABSTRACT

The present invention concerns a particulate support matrix, a solid dosage form made therefrom, and processes for making such support matrices and dosage forms, which disintegrate or dissolve in a matter of just a few seconds once placed into the oral cavity.

First, a porous particulate powder which will serve as the tablet support matrix is produced. In the second step, the pharmaceutical, for example an antihistamine, decongestant, or antibiotic is combined with the powder. Other additives may also be added to the mixture. In the third step the mixture is formed into a tablet. Finally, in the fourth step, a coating may be applied to the outer surface of the tablet to enhance the intactness and durability of the tablet.

31 Claims, No Drawings

RAPIDLY DISSOLVING DOSAGE FORM

CROSS REFERENCE TO RELATED APPLICATIONS

The present application is a continuation-in-part of U.S. Ser. No. 08/191,237, filed Feb. 3, 1994, entitled "RAPIDLY DISSOLVING ORAL DOSAGE FORM".

BACKGROUND

The present invention relates to a particulate support matrix, to rapidly dissolving solid pharmaceutical dosage forms made therefrom, and to processes of preparing such a support matrix and such a dosage form.

The recent, current and projected growth of the elderly population in the U.S. and abroad is well recognized. Currently, 12% of the U.S. population is 65 years of age or older and receives nearly 30% of the medications prescribed. It is anticipated that there may be a 10% to 60% increase in the demand for drugs by the elderly under some new government programs. In spite of the disproportionately large demand for prescription pharmaceuticals among the elderly, relatively little attention has been directed to meeting the unique pharmacotherapeutic needs of this age group. Drug products are currently designed for three groups of individuals: infants, pediatrics and adults. The needs of the infants are obviously different from those of children 2 to 12 years of age and the needs of children are obviously different from those of adults. However, the needs of the elderly population are being overlooked as they have special characteristics that necessitate dosage forms designed especially for them. Many older patients have difficulty swallowing tablets or capsules and yet the vast majority of dosage forms administered to the elderly are tablets or capsules. Uncoated tablets are convenient and economical to manufacture but are often difficult to swallow and often cause discomfort by "hanging" in the throat. Coated tablets and capsules are somewhat easier to swallow but with increasing age and the large number of drug products that are administered to a single individual, this is a source of apprehension. Liquid dosage forms are relatively easy to administer but are more costly, easily spilled, often do not taste good, occupy large volumes of space per dosage unit, and possess some inherent stability problems. As is evident, the needs of the elderly differ from those of other populations and deserve special attention in new drug development, product formulation, posology, product packaging, product labeling, patient information, and product marketing and sales. A practical and new dosage form would be of value for these patients.

Pediatric patients generally have difficulty swallowing until they reach the age of about 10–16 years old. Younger pediatric patients generally take either chewable tablets, crush and mix regular tablets with food/juice, or take a liquid dosage form. Chewable tablets, generally a good dosage form, do not always taste good. Crushing and mixing regular tablets with food or juice, is time-consuming, messy and not always practical. The difficulty of liquid dosage forms, i.e., syrups, is that they are bulky, do not always taste good, and that drugs are not as stable in a liquid dosage form as they are in a solid dosage form, such as a tablet. A practical and new dosage form would also be of value for these patients.

Incarcerated patients often will retain their medications within the oral cavity while pretending to swallow them. These can then be accumulated and taken all at once for an enhanced drug effect. Obviously, this can be very dangerous. A dosage form which would not remain intact once placed in the oral cavity would be useful when treating these patients.

There are currently several fast-dissolving products on the market. These products have a number of drawbacks including the manufacturing methods used, taste masking, and pre-versus post-loading techniques that are required. One commercially available dosage form is prepared by a lyophilization, or freeze-drying, technique which is slow and expensive. Because each "batch" of material must be handled in its entirety, the tablet cannot be produced using a continuous process where raw materials come in and finished product is output at the other end. This tablet can be either pre-loaded (i.e., the drug is added to the tablet matrix before the tablet is formed) or post loaded (the drug is added after the tablet "blank" is prepared).

One difficulty with a freeze-dried dosage form is that of taste masking. To effectively mask the taste of poorly tasting drugs, it is generally necessary to micro-encapsulate or nano-encapsulate them. Then, if they are pre-loaded, the encapsulating shell material may dissolve during the tablet production process allowing the drug to leak into the tablet matrix, resulting in a poorly tasting product. If the tablet is post-loaded, the tablet may become disfigured causing the tablet to be disposed of or handled again, adding extra expense to the process.

Another commercially available dosage form is prepared using solid state dissolution techniques. These manufacturing methods are expensive and add additional cost to the tablet. This tablet must be post-loaded. This is necessary because drugs are generally soluble in the water and alcohol which is used in the preparation of the tablet. As with the freeze-dried dosage form discussed above, when a solution of the drug is post-loaded onto the matrix blank, often the tablets become disfigured. Another problem encountered with the solid state dissolution technique is the selection of a solvent material that will evaporate quickly but will not attack the microcapsule shell surrounding the active drug.

Effervescent dosage forms contain substantial percentages of compounds for enhancing tablet breakup and dissolution which may also serve to mask the taste of certain medications. These tablets depend upon approximate stoichiometric quantities of sodium bicarbonate and an acid, e.g., citric acid or tartaric acid, reacting to form $CO_2$ to break up the tablet in the mouth. The difficulty with the commercially available effervescent tablets is that the mouth tends to "foam" leaving an uncomfortable feeling to many.

SUMMARY OF THE INVENTION

According to one aspect of the invention, there is provided a particulate matrix comprising a polymeric primary component having a predetermined net charge when in solution, a solubilizing component having a predetermined net charge when in solution of the same sign as the net charge of the primary component, and a bulking agent, characterized in that the solubilizing component has a solubility in aqueous solution greater than that of the polymeric primary component.

According to another aspect of the invention, there is provided a rapidly dissolving solid pharmaceutical dosage form comprising: a particulate support matrix comprising a polymeric primary component having a predetermined net charge when in solution, a solubilizing component having a predetermined net charge when in solution of the same sign as the net charge of the primary component, and a bulking agent, and wherein the solubilizing component has a solubility in aqueous solution greater than that of the polymeric primary component; and a pharmaceutical ingredient dispersed throughout the particulate support matrix. The support matrix is generally substantially completely disintegrable within less than about 20 seconds when the dosage form is introduced into an aqueous environment so as to release the pharmaceutical ingredient to the aqueous environment.

DESCRIPTION OF THE INVENTION

The present invention comprises a particulate support matrix, a solid dosage form made therefrom which disintegrates or dissolves in a matter of just a few seconds once placed into the oral cavity, or other aqueous environment and methods for making such support matrix and dosage form. This rapidly dissolving tablet or other solid dosage form made from the matrix described herein has many of the characteristics of a regular tablet up to the point of administration, i.e., convenient size, stable, easy to dispense, easily transportable, easy to alter the dose and easy to administer. Upon placing this dosage form in the mouth, the saliva will serve to rapidly dissolve the dosage form and the patient in effect will swallow the medication in a liquid form. The rapid-dissolving tablets of the present invention will eliminate many of the problems inherent in the other forms of orally-dissolving tablets described above since the matrix and active drug powders are blended and formed into tablets in the same way as regular tablets, except that a very light compression pressure is used in forming the tablets of the present invention.

Where used herein the term "dosage form" is meant to include any dosage form which is intended to be dissolved in any aqueous medium including water, saliva or other aqueous biological fluids or suspensions, and may include tablets, capsules, caplets, boluses, powders cachets, pills and granules.

If a drug entity has little or no taste, the dosage form will be prepared to be almost tasteless. If a drug product does have a characteristic, undesirable taste, the taste will preferably either be altered by different mechanisms such as flavorings to make it acceptable, or the drug will be micro- or nano-encapsulated with a coating that dissolves at an acidic pH and incorporated into the tablet. This rapid dissolving tablet will not only provide the geriatric, pediatric and incarcerated populations with an easy to use tablet, but may also result in long-term benefits such as enhanced patient compliance, fewer hospital admissions due to poor compliance, and enhanced health and quality of life.

Furthermore, the application of this dosage form is not limited to oral delivery as it is also applicable for use as a fast dissolving tablet when administered to other moist areas of orifices of the body, such as the rectum.

Generally, the method of the present invention comprises up to is four steps. First, a porous particulate powder which will serve as the tablet support matrix is produced. In the second step, the pharmaceutical, for example an antihistamine, decongestant, or antibiotic is combined with the powder. Other additives may also be added to the mixture. In the third step the mixture is formed into a tablet. Finally, in the fourth step, a coating may be applied to the outer surface of the tablet to enhance the intactness and durability of the tablet.

More particularly, the invention comprises a particulate support matrix for use in forming a pharmaceutical dosage form and a process for producing it. The process comprises the steps of providing an aqueous composition which further comprises (1) an aqueous medium, (2) a support agent comprising a polymeric primary component having a predetermined net charge, a solubilizing component having a predetermined net charge of the same sign as the primary component, and a bulking agent and wherein the solubilizing component has a solubility in aqueous solution greater than that of the primary component, and (3) a volatilizing agent for enhancing the rate of vaporization of the aqueous medium and for enhancing volume and porosity of the support agent during drying. The composition may contain an acidifying or alkalizing agent for setting the predetermined net charge of the components of the support agent. The primary component and solubilizing component of the support matrix may be provided in solution or may be provided in solid form and dissolved within the aqueous medium to form the aqueous composition along with the bulking agent. The aqueous composition is introduced as droplets into a drying chamber heated to a predetermined temperature causing evaporation of substantially all of the aqueous medium and volatilizing agent from the droplets. This yields the support agent as a dried and expanded particulate form comprising the particulate support matrix.

The primary polymer component and the solubilizing component may have net charges which are closer to a neutral pH than is preferable for optimal rapid dissolution. For example, when the primary polymer component is an acidic gelatin, and the solubilizing polymer component an acidic gelatin hydrolysate, the isoelectric points may be higher than the preferred pH, which is below 5.5. In such a case, it is desired to reduce the pH of the solution to a preferred pH by the addition of an acidifying agent, such as citric acid or acetic acid. This will shift the isoelectric points of the gelatin to pH levels within the preferred range and will maintain them at such pH during the drying process.

However, when the primary polymeric component and the solubilizing polymeric component have isoelectric pHs in their native form which are within the preferred pH range of about 3.5 to 5.5, it may be unnecessary to add an acidifying agent to the aqueous composition. For example, if the polymeric components are polypeptides comprising a preponderance of acidic amino acids, the polypeptides may have isoelectric points which are sufficiently low. Similarly, if the polypeptides comprise a preponderance of basic amino acids, the polypeptides may have isoelectric points sufficiently basic to eliminate the need for an alkalizing agent to raise the pH of the aqueous composition.

After the net charge of the primary and solubilizing components is altered (when necessary) either by an acidifying agent or by an alkalizing agent, the altered net charge will be maintained by the polymeric components due to their natural buffering capacity.

The completed particulate support matrix comprises (1) a polymeric primary component having a net charge when in solution, (2) a solubilizing component having a net charge when in solution of the same sign as the net charge of the primary component, and (3) a bulking agent. The solubilizing component has a solubility in aqueous solution greater than that of the polymeric primary component for enhancing dissolution of the particulate support matrix upon exposure to an aqueous environment. When the support matrix is introduced into an aqueous environment it is substantially completely disintegrable within less than about 20 seconds. The support matrix may be substantially completely disintegrable within less than about 10 seconds, or more preferably within from about 1 second to about 6 seconds. The particulate support matrix preferably has a bulk density within a range of about 0.03 g/ml to about 0.06 g/ml. The particulate support matrix may have a bulk density within a range of from 0.03 g/ml to about 0.3 g/ml.

The polymeric primary component may comprise a first polypeptide and the solubilizing component may comprise a second polypeptide. More preferably, the first polypeptide may be a nonhydrolyzed gelatin and the second polypeptide may be a hydrolyzed gelatin. Both the first polypeptide and the second polypeptide may have a net positive charge. Alternatively, the first polypeptide and the second polypeptide may have a net negative charge. The particulate support matrix may further comprise an agent for maintaining the net charge of the primary support component and the solubilizing component when it is desired to maintain the net charges at pHs different from those of the pH of the native primary and solubilizing components in solution.

The invention further comprises a rapidly dissolving solid pharmaceutical dosage form, which is made from an active ingredient such as a pharmaceutical product which is mixed and dispersed throughout the particulate support matrix described herein and then formed into a tablet. When this dosage form is introduced into an aqueous environment the support matrix is substantially completely disintegrable within less than about 20 seconds so as to release the pharmaceutical ingredient to the aqueous environment. The support matrix may be substantially completely disintegrable within less than about 10 seconds, or more preferably in from about 1 second to about 6 seconds. The dosage form may also contain a small amount of an effervescing agent (generally from 0 to 5% of weight and preferably less than about 3%) for aiding in the initial phase of disintegration of the dosage form, a binding agent, and a flavoring agent. Further, the dosage form may have a polymeric coating of the external surface for enhancing the intactness of the dosage form. The density of the dosage form is generally within a range of about 0.1 g/ml to about 0.2 g/ml.

Preparation of the Particulate Support Matrix

The particulate support matrix, in the preferred embodiment, is produced using standard spray-drying techniques, well known to persons of ordinary skill in the art. The components of the composition which is used to produce the matrix include a support agent which comprises in one version a gelatin and a hydrolyzed gelatin and additionally a bulking agent for increasing the bulk and solubility of the support matrix and tablet formed therefrom. Another component is a volatilizing agent, having a volatility which exceeds that of water, such as an alcohol, preferably ethanol. Another optional component is an acidifying or alkalizing agent which functions to cause the components of the support agent to be maintained with a net charge, either positive (when the preferred pH of the composition is below neutral) or negative (when the preferred pH is above neutral). In a preferred version the support matrix is maintained with a net positive charge by an acidic agent such as citric acid. The composition further comprises an aqueous medium such as water.

Critical physical factors in the spray drying process have to do with net charge and solubility of the support agent (for example, of proteins) and the evaporation characteristics of the volatilizing agent (for example, ethanol). In the preferred embodiment, the support agent is comprised of a polymeric primary component and a solubilizing component and a bulking agent. The solubilizing component contributes to the support function of the support matrix when in the dried particulate but also serves to enhance the rate of dissolution of the support matrix once the tablet is introduced into an aqueous environment such as the salivary environment of the oral cavity. In one example of the preferred embodiment, the primary and solubilizing components of the support agent comprise two different forms of gelatin, an unmodified form (the polymeric primary component), and a hydrolyzed form (the solubilizing component), and act together to form a support matrix in the dried particles. Both of these forms of gelatin are commercially available. The hydrolyzed gelatin assists the unmodified gelatin as a structural component of the matrix but it also functions to increase the solubility of the matrix, in some cases by a factor of two. In an experiment where the particulate matrix was formed only from gelatin, water and alcohol, the powder dissolved in approximately 25 seconds. When hydrolyzed gelatin was added to the formula, the powder produced therefrom dissolved in about 15 seconds.

In the preferred version of the invention, the solution of the protein and protein hydrolysate is made acidic, preferably in the pH range of about 3.5 to 5.5, and more preferably from about 4.0 to about 5.0. This acidity causes the protein components of the composition to have a net positive charge at a pH which enhances repulsion of the protein components. Together with or in lieu of gelatins, the primary support component and/or solubilizing component may be comprised of polymers, including acacia, alginic acid, pectin, tragacanth, and xanthan gum.

The following are examples of pairs of polymeric primary support and solubilizing components (respectively) (1) acacia and pectin, 2:1; and (2) tragacanth and xanthan gum, 1:3. The above ratios are approximate.

The effect of the net positive charge of the protein molecules is to cause individual protein molecules to be repellent to each other when in solution thereby reducing the tendency for the protein molecules to "cling" to each other. As a result, the protein molecules tend to remain repelled in the solution and during the spray drying process while the droplets of the composition are drying into particles. As a result, the powder formed will be of relatively low bulk density, generally in the range of from about 0.03 g/ml to about 0.06 g/ml. The bulking agent contributes to the bulk and stability of the support matrix and increases the rate at which the support matrix will dissolve. Examples of bulking agents are carbohydrates such as mannitol, sorbitol, sucrose, lactose, xylitol, and acacia. Mannitol and sorbitol are preferred bulking agents.

The incorporation of the ethanol (or another volatilizing agent) into the solvent system functions to decrease the vaporization temperature of the solvent and contributes to the production of a more porous particle having a lesser bulk density and thus a greater bulk volume. It has been discovered that if water alone is used as the aqueous solvent, when the composition is introduced as droplets into the spray drying chamber, the droplets will have a tendency to contract in size thus increasing in density, as they traverse from the spray nozzle, through the drying chamber, to the collecting chamber of the spray-drier unit. By incorporating into the solvent a volatilizing agent such as ethanol, numerous pores and channels are formed within the structure of the droplet as the solvent mixture volatilizes from the droplet during the drying process. The particle formed from the droplet retains a higher porosity and low density and even experiences expansion resulting in a powder having a larger bulk volume.

In one experiment, a control comprising a quantity of a formula excluding ethanol produced a dried particulate support matrix powder having a bulk density of 0.077 g/ml (specific bulk volume was about 13 ml/g) and a bulk volume of 180 ml. The treatment comprised a comparable initial quantity of the formula with ethanol added produced a dried particulate support matrix powder having a bulk density of 0.049 g/ml (specific bulk volume was about 20.4 ml/g) and a bulk volume of 450 ml. The formula comprised, mannitol (10 g), sorbitol (5 g), citric acid (0.4 g), sucrose (0.15 g), Explotab® (0.15 g). gelatin G8-275 (1 g). gelatin hydrolysate (1 g), and a quantity of water sufficient to produce a volume of 500 ml. The amount of ethanol added to the treatment was 150 ml.

The term "bulk volume", as used herein, is defined as the actual volume of a quantity of a quantity of particulate support matrix material. The term "true volume" as used herein is defined as the volume of a quantity of particulate support matrix material after that quantity has been compacted to eliminate the void space of the quantity. The term "bulk density" as used herein is defined as the mass of a quantity of the particulate support material divided by the bulk volume of that quantity. The term "specific bulk volume" is defined as the bulk volume of a quantity of particulate support material divided by the mass of that quantity. The term "porosity" as used herein is a percentage defined as:

$$\frac{\text{bulk volume} - \text{true volume}}{\text{bulk volume}} \times 100.$$

This result of a product having a greater bulk volume when ethanol is added is apparently obtained by the lowering of the vaporization temperature of the solvent thus increasing the rate at which the solvent is vaporized. The retention of the porous nature of the particle is critical to the speed with which a tablet constructed of the material dissolves. The porosity enhances the capillary movement of saliva into the interior of the tablet thereby increasing the dissolution rate of the support matrix of the tablet.

The acidifying or alkalizing agent, when present in the composition serves to maintain the net charge of the molecules of the support matrix. For example, in one preferred embodiment, the predetermined net positive charge of the protein components is set by an acidifying agent such as citric acid. When the support matrix makes contact with an aqueous solution the proteins comprising the support matrix will have a positive charge and immediately repel each other as soon as they dissolve, thus causing the particles of the tablet to repel each other, enhancing the rapidness of disintegration of the tablet. A similar phenomenon may be effected by using an alkalizing agent such as sodium bicarbonate as an alkalizing agent (causing the polypeptide components of the support matrix to be negatively charged).

In the present invention, the primary and solubilizing components of the support matrix together generally comprise from 2–20% of the dry components of the aqueous composition (percentage by weight, when the composition comprises the primary and solubilizing components, the bulking agent and, optionally, the buffering agent) used to form the particulate support matrix. More preferably, the range is from 3–18% and more preferably is from 6–16%. Most preferably the primary and solubilizing components of the support matrix together comprise from 10–14% of dry portion of the aqueous composition.

In addition, the bulking agent of the support matrix generally comprises from 60–96% of the dry components of the aqueous composition (percentage by weight) used to form the particulate support matrix. More preferably, the range is from 75–92% and more preferably is from 80–90%. Most preferably the bulking agent of the support matrix comprises from 82–88% of the dry portion of the aqueous composition. In addition, the acidifying or alkalizing agent of the support matrix generally comprises from 0–30% of the dry components of the aqueous composition (percentage by weight) used to form the particulate support matrix. More preferably, the range is from 1–16% and more preferably is from 1–6%. Most preferably the acidifying or alkalizing agent of the support matrix comprises from 1–3% of the dry portion of the aqueous composition.

Formation of the Tablet

Before forming the particulate support matrix into a tablet, a quantity of the drug, medication, or pharmaceutical and any necessary flavoring agent is added to a quantity of the particulate support matrix. The optional addition of a small amount of effervescent material serves to assist in the initial stage of the disintegration of the particles of the tablet. The tablet may be formed by methods known to those of ordinary skill in the art. For example, the tablet may be formed by direct compression. Or, it may be formed by first adding a moistening agent such as alcohol, then compressing or molding the composition. Or, it may be formed by first adding a binding agent such as polyvinylpyrrolidone, then compressing or molding the composition into a tablet. The dosage form described herein may include one or more adjuvants which can be chosen from those known in the art including flavors, diluents, colors, binders, fillers, compaction vehicles, effervescent agents, and non-effervescent disintegrants, such as those disclosed in U.S. Pat. No. 5,178,878, issued to Wheling et al. on Jan. 12, 1993, and in U.S. Pat. No. 5,215,756, issued to Gole et al., on Jun. 1, 1993, the specifications of which are hereby incorporated herein by reference. More specifically, the tablets may be composed of, but not limited to, the following: gelatin (commercially available Pharmagel® A and B, Type A, 275 Bloom, and Type B, 100 Bloom), hydrolyzed gelatin, sugars (mannitol, sucrose), organic acids (citric acid, succinic acid), sodium bicarbonate, ethyl alcohol, disintegrants such as Explotab® (sodium starch glycollate) and AcDiSol® (modified cellulose gum), starch, polyvinylpyrrolidone polymers, alginic acid, bulking and electrical charge agents such as acacia, and polyethylene glycol polymers.

Following the formation of the mixture into a tablet, it may be desired to apply a very thin coating to the external surface of the tablet. The function of the coating, when applied, is to enhance the intactness of the tablet. Due to the porous nature of the tablet, the tablet tends to be rather fragile and breakable and generally benefits from the added protection afforded by the coating. The coating may comprise a polymer, such a polyvinyl alcohol or a polyvinylpyrrolidone, which, when applied forms a polymeric "net" over and into the tablet. This "net" maintains the tablet intact but does not inhibit the capillary uptake by the tablet once placed in the aqueous environment of the oral cavity although dissolution time may be slightly increased when a coating is applied to the tablet (see Example 17).

In preparation for forming the tablets, a tablet blend is produced by combining a quantity of the particulate support matrix with a quantity of the pharmaceutical or drug and optionally with a quantity of an effervescent blend, a binding solution and/or a flavoring.

The pharmaceutical composition can be added at several different stages of the formulation of the dosage form depending on the circumstances. The pharmaceutical can be added directly to the liquid composition before or during the spray drying process at the inlet nozzle. The resulting product can then be incorporated into the tablets. Alternatively, the pharmaceutical, in untreated or encapsulated form, is mixed with the particulate support matrix (after the spray drying process, before or after adding the binder, if a binder is added) and then formed into tablets. Alternatively, the pharmaceutical could be added by direct application to the preformed tablet by spray coating or drop coating.

As noted, the addition of the effervescent blend, the binding solution (also referred to herein as the binding agent) and the flavoring are optional. When present, the binding solution and the effervescent blend may be added to the support matrix powder in a ratio of about 20:10:1 (support matrix:binding solution: effervescent blend). The effervescent blend consists of an approximately stoichiometric ratio of citric/tartaric acids with sodium bicarbonate in a powder form. In various versions, the effervescent blend may comprise the following ratios of components:

(1) citric acid:sodium bicarbonate, 1:1.2
(2) tartaric acid:sodium bicarbonate, 2:2.24
(3) citric acid:tartaric acid:sodium bicarbonate, 1:2:3.4

The blend is slightly acidic so there will be a slight tartness in the mouth upon dissolution of the product. As is indicated above, the amount of effervescent blend present is minimal (from 0 to 5% of total weight) and its fizzing properties are almost non-detectable in the mouth. Its presence enhances the separation of the porous particles and enhances capillarity during dissolution of the tablet within the oral cavity thereby decreasing dissolution time of the tablet (see Example 15). The effervescent blend also enhances salivation in the oral cavity.

The binding solution in one version of the invention consists of 1% PVP-40 in ethanol (e.g., see Example 14). Other binding solutions may consist of mixtures of PEG 1000 and PEG 4000 in alcohol, PEG 1000 and PVP 1000 in alcohol. Acetone may be substituted for ethanol or other alcohols in these formulations. The binding solution may further comprise a quantity of a surface active agent such as sodium lauryl sulfate for further increasing the dissolution rate of the dosage form. The binding solution, when used, is mixed slowly with the spray dried powder, then dried at about 40°–50° C.

In one method used for forming the tablets, a quantity of the tablet blend is lightly compressed. The tablets thus produced are then coated with a very thin coating of an organic solution of a polymer, which rapidly evaporates leaving a polymeric "net" on the surface of the tablet. This thin external "net" aids in keeping the tablets intact during handling. Polymers may include, but not be limited to PVP and PVA. The coating may be applied by passing the tablet into a chamber having a saturated atmosphere of the coating material. Alternatively, the coating may be applied by lightly spraying the coating material onto the surface of the tablet.

In another method for forming the tablets, a quantity of the tablet blend is moistened with ethanol then passed through a #40 mesh screen and immediately compressed into tablets and dried overnight at about 50° C. The tablets thus produced may be then coated with a very thin coating of an organic solution of a polymer, which rapidly evaporates leaving a "net" on the surface of the tablet.

The present invention contemplates a tablet which is much lighter (for example 50 mg) than a comparable typical commercially available tablet (for example 400–500 mg).

The present invention further contemplates a tablet which will disintegrate within the oral cavity in less than about 20 seconds. More preferably, the tablet will disintegrate within less than about 10 seconds. More preferably, the tablet will disintegrate within the oral cavity in less than about 6 seconds. Still more preferably, the tablet will disintegrate in from about 1 second to about 4 seconds. The bulk density of the formed tablet is preferably in a range of from about 0.1 g/ml to about 0.2 g/ml, but may be either less or greater than the bounds of this range. Porosity may be in a range of from about 50 to 75% in a preferred embodiment.

EXAMPLES

The following examples further illustrate compositions of the dosage form of the present invention including preferred versions and methods of making the same; however these examples are not to be construed as limitations of this invention.

Standardized Dissolution Testing method

The testing method used to determine the dissolution of the tablet material is a modification of the USP disintegration method which involves the agitation of tablets in purified water at 37° C. The present testing conditions used a 600 ml glass beaker with water at about 37° C. The surface of the water was motionless. The water was not agitated. A fresh beaker of water was used for each test. To test the dissolution rate of the particulate matrix in powder form, the tip of a 4" stainless steel spatula was dipped into the powder and a quantity of powder equivalent to approximately 100 mg was removed from the container and dropped onto the surface of the water from a distance of approximately 2.5 cm (1 inch). To test the dissolution rate of the support matrix in tablet form, a tablet was removed from its container and placed on the tip of a 4" stainless steel spatula. The tip of the spatula was held approximately 2.5 cm (1 inch) above the surface of the water and the tablet allowed to slide off the spatula tip onto the water. The testing method is an approximation of the in vitro use of the tablet. In actual practice, of course, the tablet will be placed on the tongue and a combination of the saliva dissolving the tablet and the tongue action aiding in its breakup will occur.

Where used herein, the term "substantially completely disintegrable" means that the dosage form is dissolved in solution such that it is virtually entirely dispersed into the solution. This does not necessarily imply total disintegration or dispersion. Disintegration time is the time from immersion for substantially complete dispersion of the tablet as determined by visual observation. As used herein, the term "substantially completely disintegrable" does not require dissolution or disintegration of all microcapsules or other discrete inclusions of the dosage form, for some of these may be more slowly soluble than the particulate matrix which comprises the critical dissolution enhancing component of the dosage form.

EXAMPLE 1

The following components were added to a quantity of purified water sufficient to produce a mixture with a volume of 500 ml and a pH of 2.8:

| | |
|---|---|
| Mannitol | 30.0 g |
| Gelatin G8-275 | 1.2 g |
| Gelatin Hydrolysate | 1.2 g |
| Explotab ® (Sodium Starch Glycolate, NF) | 0.6 g |
| Acacia | 0.6 g |
| PVP-10 | 0.3 g |
| Citric acid | 1.5 g |
| Tartaric acid | 1.5 g |
| Ethanol | 150 ml |

The mixture was introduced into a Buchi model 190 spray drier with a heat setting of 10, an aspirator setting of 5, a flow rate setting of 4.27, an initial flow control setting of 700 (changing to 650 after the first time interval), and a vacuum setting of −20. Chamber temperatures were measured at approximately 5 minute consecutive intervals during the drying process. The temperatures at the flow inlet point were 69° C. (156° F.), 69° C. (156° F.), 71° C. (159° F.), 68° C. (154° F.) and 69° C. (157° F.). The temperatures at the flow outlet point (the point where the dried product exits the drying chamber to product collector) were measured as 46°

C. (115° F.), 44° C. (111° F.), 30° C. (86° F.), 43° C. (109° F.), and 42° C. (108° F.). The particulate support matrix product had a bulk volume of about 140 ml, a specific bulk volume of 5.6 ml/g and a porosity of 59.6%. The resulting matrix had a dissolution time of from 5 to 15 seconds.

EXAMPLE 2

The following components were added to a quantity of purified water sufficient to produce a mixture with a volume of 500 ml and a pH of 6.4:

| Sucrose | 30.0 g |
| Gelatin G8-275 | 0.9 g |
| Gelatin Hydrolysate | 0.9 g |
| Explotab ® | 0.5 g |
| Ethanol | 150 ml |

The mixture was introduced into a Buchi model 190 spray drier with a heat setting of 10, an aspirator setting of 5 (which was changed to 7 after the second time interval), a flow rate setting of 4.27, a flow control setting of 700, and a vacuum setting of −20. Chamber temperatures were measured at approximately 5 minute consecutive intervals during the drying process. The temperatures at the flow inlet point were 68° C. (154° F.), 68° C. (154° F.), 56° C. (133° F.), 62° C. (143° F.), and 62° C. (143° F.). The temperatures at the flow outlet point (the point where the dried product exits the drying chamber to product collector) were measured as 40° C. (104° F.), 40° C. (104° F.), 32° C. (90° F.), 34° C. (93° F.), 34° C. (93° F.), and 34° C. (93° F.). The particulate support matrix product had a bulk volume of about 100 ml, a specific bulk volume of 2.3 ml/g and a porosity of 8.8%. Dissolution time of the support matrix was 5-15 seconds.

EXAMPLE 3

The following components were added to a quantity of purified water sufficient to produce a mixture with a volume of 400 ml and a pH of 8.4:

| Mannitol | 60 g |
| Gelatin G8-275 | 1.2 g |
| Gelatin Hydrolysate | 1.2 g |
| Acacia | 0.4 g |
| Explotab ® | 0.4 g |
| Alginic Acid | 0.4 g |
| PVP-40 | 0.6 g |
| Sodium Bicarbonate | 2.4 g |
| Ethanol | 120 ml |

The mixture was introduced into a Buchi model 190 spray drier with a heat setting of 10, an aspirator setting of 5, a flow rate setting of 4.27, an initial flow control setting of 700 (changing to 550 after the first time interval), and a vacuum setting of −20. Chamber temperatures were measured at approximately 5 minute consecutive intervals during the drying process. The temperatures at the flow inlet point were 68° C. (154° F.), 69° C. (157° F.), 69° C. (157° F.), 69° C. (157° F.), and 69° C. (157° F.). The temperatures at the flow outlet point (the point where the dried product exits the drying chamber to product collector) were measured as 42° C. (107° F.), 42° C. (108° F.), 42° C. (108° F.), 42° C. (108° F.), and 42° C. (108° F.). The particulate support matrix product had a bulk volume of about 60 ml, a specific bulk volume of 3.7 ml/g and a porosity of 38.8%. Dissolution time of the matrix was about 5 seconds.

EXAMPLE 4

The following components were added to a quantity of purified water sufficient to produce a mixture with a volume of 400 ml and a pH of 3.0:

| Mannitol | 60 g |
| Gelatin G8-275 | 1.2 g |
| Gelatin hydrolysate | 1.2 g |
| Acacia | 0.8 g |
| Explotab ® | 0.4 g |
| PVP-40 | 0.6 g |
| Citric acid | 0.9 g |
| Tartaric acid | 0.9 g |
| Ethanol | 120 ml |

The mixture was introduced into a Buchi model 190 spray drier with a heat setting of 10, an aspirator setting of 5, a flow rate setting of 4.27, an initial flow control setting of 700 (changing to 600 after the first time interval and to 550 after the second time interval), and a vacuum setting of −20. Chamber temperatures were measured at approximately 5 minute consecutive intervals during the drying process. The temperatures at the flow inlet point were 68° C. (155° F.), 66° C. (150° F.) and 68° C. (155° F.). The temperatures at the flow outlet point (the point where the dried product exits the drying chamber to product collector) were measured as 46° C. (114° F.), 43° C. (109° F.) and 42° C. (108° F.). The particulate support matrix product had a bulk volume of about 70 ml, a specific bulk volume of 5.11 ml/g and a porosity of 55.7%. Dissolution time of the support matrix was from 2-10 seconds.

EXAMPLE 5

The following components were added to a quantity of purified water sufficient to produce an acidic mixture "Part A" with a volume of 100 ml:

| Mannitol | 20.0 g |
| PVP-10,000 | 1.1 g |
| Citric Acid | 3.8 g |
| Ethanol | 20.0 ml |

The following components were added to a quantity of purified water to produce a basic mixture "Part B" with a volume of 100 ml:

| Mannitol | 20.0 g |
| PVP-10,000 | 1.1 g |
| Sodium bicarbonate | 5.0 g |
| Ethanol | 20.0 ml |

The two mixtures were mixed as introduced into a Buchi model 190 spray drier with the heat settings shown below, aspirator settings shown below, a flow rate setting of 4.27, a flow control setting of 700, and a vacuum setting of −20, as shown below. Chamber temperatures were measured at approximately 5 minute consecutive intervals during the drying process. These temperatures are shown as inlet and outlet readings below. The particulate support matrix product had a bulk volume of about 50 ml and a porosity of 31.2%.

| Heating Inlet, | 10 | 11 | 12 | 10 | 12 | 12 | 15 | 14 |
|---|---|---|---|---|---|---|---|---|
| °C. | 49 | 72 | 90 | 87 | 104 | 102 | 107 | 108 |
| °F. | 121 | 162 | 194 | 188 | 220 | 215 | 225 | 226 |
| Outlet, | | | | | | | | |
| °C. | 36 | 37 | 37 | 37 | 39 | 40 | 41 | 41 |
| °F. | 96 | 98 | 98 | 98 | 102 | 104 | 106 | 106 |
| Aspirator | 6 | 6 | 6 | 6 | 15 | 15 | 20 | 20 |

EXAMPLE 6

The following components were added to a quantity of purified water sufficient to produce an acidic mixture "Part A" with a volume of 100 ml:

| Mannitol | 22.5 g |
|---|---|
| Gelatin 275 | 0.46 g |
| Citric Acid | 3.8 g |
| Ethanol | 30.0 ml |

The following components were added to a quantity of purified water to produce a basic mixture "Part B" with a volume of 200 ml:

| Mannitol | 22.5 g |
|---|---|
| Gelatin 275 | 0.46 g |
| Sodium Bicarbonate | 5.0 g |
| Ethanol | 30.0 ml |

The mixture was introduced into a Buchi model 190 spray drier with heat settings shown below, aspirator settings shown below, a flow rate setting of 4.27, a flow control setting of 700, and a vacuum setting of −30. Chamber temperatures were measured at approximately 5 minute consecutive intervals during the drying process. The temperatures at the flow inlet point and outlet point are shown below. The particulate support matrix product had a bulk volume of about 70 ml and a porosity of 35.9% and a dissolution time of from 6–10 seconds.

| Heating Inlet, | 5 | 6 | 9 | 10 | 11 | 12 |
|---|---|---|---|---|---|---|
| °C. | 33 | 34 | 38 | 66 | 66 | 79 |
| °F. | 92 | 94 | 100 | 150 | 150 | 175 |
| Outlet, | | | | | | |
| °C. | 22 | 24 | 28 | 47 | 48 | 42 |
| °F. | 71 | 76 | 83 | 117 | 118 | 108 |
| Aspirator | 5 | 6 | 10 | 12 | 10 | 12 |

EXAMPLE 7

The following components were added to a quantity of purified water sufficient to produce a mixture with a volume of 300 ml and a pH of 3.0:

| Mannitol | 30.0 g |
|---|---|
| Gelatin G8-275 | 0.9 g |
| Gelatin Hydrolysate | 0.9 g |
| Explotab ® | 0.6 g |
| Tartaric Acid | 1.8 g |
| Ethanol | 90 ml |

The mixture was introduced into a Buchi model 190 spray drier with a heat setting of 10, an aspirator setting of 5, a flow rate setting of 4.27, an initial flow control setting of 700 (changing to 650 after the first time interval), and a vacuum setting of −20. Chamber temperatures were measured at approximately 5 minute consecutive intervals during the drying process. The temperatures at the flow inlet point were 69° C. (156° F.), 69° C. (156° F.), 69° C. (156° F.), 69° C. (156° F.), and 68° C. (155° F.). The temperatures at the flow outlet point (the point where the dried product exits the drying chamber to product collector) were measured as 46° C. (114° F.), 42° C. (108° F.), 33° C. (92° F.), 32° C. (89° F.), and 29° C. (84° F.). The particulate support matrix product had a bulk volume of about 150 ml, a specific bulk volume of about 6.3 ml/g and a porosity of 64.0%. Dissolution time of the support matrix was about 5–15 seconds.

EXAMPLE 8

The following components were added to a quantity of purified water sufficient to produce a mixture with a volume of 500 ml and a pH of 8.7:

| Mannitol | 30 g |
|---|---|
| Gelatin G8-275 | 1.2 g |
| Gelatin Hydrolysate | 1.2 g |
| Acacia | 0.6 g |
| Explotab ® | 0.6 g |
| PVP-40 | 0.3 g |
| Sodium Bicarbonate | 3.0 g |
| Ethanol | 150 ml |

The mixture was introduced into a Buchi model 190 spray drier with a heat setting of 10, an aspirator setting of 5, a flow rate setting of 4.27, an initial flow control setting of 700 (changing to 650 after the first time interval), and a vacuum setting of −20. Chamber temperatures were measured at approximately 5 minute consecutive intervals during the drying process. The temperatures at the flow inlet point were 71° C. (160° F.), 69° C. (157° F.), 69° C. (157° F.), 69° C. (156° F.), and 68° C. (155° F.). The temperatures at the flow outlet point (the point where the dried product exits the drying chamber to product collector) were measured as 46° C. (115° F.), 42° C. (108° F.), 42° C. (107° F.), 42° C. (108° F.), and 42° C. (108° F.). The particulate support matrix product had a relatively small bulk volume of 70 ml, a specific bulk volume of about 3.9 ml/g and a porosity of 41.5%. Dissolution time was about 5–20 seconds.

EXAMPLE 9

The following components were added to a quantity of purified water sufficient to produce a mixture with a volume of 500 ml and a pH of 3.5:

| Mannitol | 30 g |
|---|---|
| Gelatin G8-275 | 0.9 g |
| Gelatin Hydrolysate | 0.9 g |
| Explotab ® | 0.6 g |
| Sucrose | 1.5 g |

| | |
|---|---|
| Citric Acid | 0.45 g |
| Ethanol | 150 ml |

The mixture was introduced into a Buchi model 190 spray drier with a heat setting of 10, an aspirator setting of 7, a flow rate setting of 4.27, an initial flow control setting of 700 (changing to 670 after the third time interval), and a vacuum setting of −20. Chamber temperatures were measured at approximately 5 minute consecutive intervals during the drying process. The temperatures at the flow inlet point were 69° C. (156° F.), 68° C. (155° F.), 69° C. (156° F.), 68° C. (155° F.), and 68° C. (155° F.). The temperatures at the flow outlet point (the point where the dried product exits the drying chamber to product collector) were measured as 47° C. (117° F.), 45° C. (113° F.), 41° C. (106° F.), 42° C. (108° F.), and 42° C. (107° F.). The particulate support matrix product had a bulk volume of about 175 ml with a specific bulk volume of 6.6 ml/g and a porosity of 65.6%. Dissolution time was 3–4 seconds.

EXAMPLE 10

The following components were added to a quantity of purified water sufficient to produce a mixture with a volume of 1000 ml and a pH of 4.5:

| | |
|---|---|
| Mannitol | 16.0 g |
| Gelatin G8-275 | 2.0 g |
| Gelatin Hydrolysate | 2.0 g |
| Explotab ® | 0.6 g |
| PVP-40 | 0.16 g |
| Sucrose | 0.41 g |
| Citric acid | 0.33 g |
| Ethanol | 300 ml |

The mixture was introduced into a Buchi model 190 spray drier with a heat setting of 9, an aspirator setting of 6 (changing to 7 after the first time interval), a flow rate setting of 5, an initial flow control setting of 700 (changing to 600 after the first time interval and to 500 after the fourth time interval), and a vacuum setting of −20. Chamber temperatures were measured at approximately 5 minute consecutive intervals during the drying process. The temperatures at the flow inlet point were 59° C. (139° F.), 62° C. (143° F.), 62° C. (144° F.), 62° C. (144° F.), and 61° C. (142° F.). The temperatures at the flow outlet point (the point where the dried product exits the drying chamber to product collector) were measured as 39° C. (102° F.), 34° C. (94° F.), 36° C. (97° F.), 40° C. (104° F.), and 34° C. (94° F.). The particulate support matrix product had a bulk volume of about 150 ml, a specific bulk volume of 8.7 ml/g and a porosity of 73.9%. Dissolution time was about 5–15 seconds.

EXAMPLE 11

The following components were added to a quantity of purified water sufficient to produce a mixture with a volume of 500 ml and a pH of 4.3:

| | |
|---|---|
| Mannitol | 15 g |
| Gelatin G8-275 | 1.0 g |
| Gelatin Hydrolysate | 1.0 g |
| Explotab ® | 0.6 g |
| Ac Di Sol ® | 0.3 g |
| (Modified Cellulose Gum, NF) | |
| Sucrose | 0.3 g |
| Citric Acid | 0.3 g |
| Ethanol | 150 ml |

The mixture was introduced into a Buchi model 190 spray drier with a heat setting of 9, an aspirator setting of 6, a flow rate setting of 5, a flow control setting of 620, and a vacuum setting of −20. Chamber temperatures were measured at approximately 5 minute consecutive intervals during the drying process. The temperatures at the flow inlet point were 64° C. (148° F.), 64° C. (147° F.), 64° C. (147° F.), 64° C. (147° F.), and 64° C. (147° F.). The temperatures at the flow outlet point (the point where the dried product exits the drying chamber to product collector) were measured as 47° C. (116° F.), 41° C. (105° F.), 39° C. (103° F.), 39° C. (102° F.), and 39° C. (102° F.). The particulate support matrix product had a bulk volume of about 100 ml, a specific bulk volume of about 7.5 ml/g and a porosity of 69.8%. Dissolution time was 5–10 seconds.

EXAMPLE 12

The following components were added to a quantity of purified water sufficient to produce a mixture with a volume of 500 ml and a pH of 4.10:

| | |
|---|---|
| Sucrose | 15.0 g |
| Gelatin G8-275 | 1.0 g |
| Gelatin Hydrolysate | 1.0 g |
| Citric Acid | 0.3 g |
| Explotab ® | 0.58 g |
| Ethanol | 150 ml |

The mixture was introduced into a Buchi model 190 spray drier with a heat setting of 9, an aspirator setting of 6, a flow rate setting of 5, an initial flow control setting of 700 (changing to 650 after the second time interval), and a vacuum setting of −20. Chamber temperatures were measured at approximately 5 minute consecutive intervals during the drying process. The temperatures at the flow inlet point were 68° C. (154° F.), 64° C. (148° F.), 63° C. (145° F.), 63° C. (145° F.), 63° C. (145° F.) and 64° C. (147° F.). The temperatures at the flow outlet point (the point where the dried product exits the drying chamber to product collector) were measured as 40° C. (104° F.), 40° C. (104° F.), 37° C. (98° F.), 35° C. (95° F.), 35° C. (95° F.) and 37° C. (98° F.). The very hygroscopic particulate support matrix product having a bulk volume of about 100 ml, a specific bulk volume of about 4.05 ml/g and a porosity of 44.1% was obtained. Dissolution time was 5–15 seconds.

EXAMPLE 13

The following components were added to a quantity of purified water sufficient to produce a mixture with a volume of 500 ml and a pH of 4.0:

| | |
|---|---|
| Sorbitol | 15.0 g |
| Mannitol | 15.0 g |
| Gelatin G8-275 | 1.0 g |
| Gelatin Hydrolysate | 1.0 g |

-continued

| | |
|---|---|
| Explotab ® | 0.6 g |
| Citric Acid | 0.34 g |
| Ethanol | 150 ml |

The mixture was introduced into a Buchi model 190 spray drier with a heat setting of 8, an aspirator setting of 6, a flow rate setting of 5, an initial flow control setting of 700 (changing to 600 after the first time interval), and a vacuum setting of −20.

Chamber temperatures were measured at approximately 5 minute consecutive intervals during the drying process. The temperatures at the flow inlet point were 55° C. (131° F.), 55° C. (131° F.), 55° C. (131° F.), 55° C. (131° F.), 55° C. (131° F.) and 55° C. (131° F.). The temperatures at the flow outlet point (the point where the dried product exits the drying chamber to product collector) were measured as 34° C. (94° F.), 34° C. (94° F.), 34° C. (94° F.) 95° F., 35° C. (95° F.) and 35° C. (95° F.). A granular particulate support matrix product having a bulk volume of about 250 ml, a specific bulk volume of about 6.8 ml/g and a porosity of 66.5% was obtained. Dissolution time was about 2–3 seconds.

EXAMPLE 14

The following components were added to a quantity of purified water sufficient to produce a mixture with a volume of 1000 ml and a pH of 4.5.

| | |
|---|---|
| Mannitol | 15.0 g |
| Sorbitol | 15.0 g |
| Gelatin G8-275 | 2.0 g |
| Gelatin Hydrolysate | 2.0 g |
| Explotab ® | 0.8 g |
| Citric Acid | 0.7 g |
| PVP-40 | 0.3 g |
| Sucrose | 0.6 g |
| Ethanol | 300 ml |

The mixture was introduced into a Buchi model 190 spray drier with a heat setting of 8, changing to 8.5 after the second time interval, an aspirator setting of 6, a flow rate setting of 5, a flow control setting of 700, and a vacuum setting of −20. Chamber temperatures were measured at approximately 5 minute consecutive intervals during the drying process. The temperatures at the flow inlet point were 59° C. (139° F.), 55° C. (131° F.), 61° C. (141° F.), 59° C. (138° F.), 58° C. (137° F.), 136° F. and 58° C. (137° F.). The temperatures at the flow outlet point (the point where the dried product exits the drying chamber to product collector) were measured as 36° C. (96° F.), 32° C. (89° F.), 34° C. (93° F.), 33° C. (92° F.), 34° C. (93° F.), 34° C. (93° F.) and 34° C. (93° F.). The particulate support matrix product had a bulk volume of about 300 ml, a specific bulk volume of about 12.7 ml/g and a porosity of 82.1%. Dissolution time was 1–5 seconds. When a binding agent (PVP-40, 0.3 g) was added to a particulate matrix produced from this mixture, the dissolution time was 2–5 seconds in tablet form.

EXAMPLE 15

The following components were added to a quantity of purified water sufficient to produce a mixture with a volume of 1000 ml and a pH of 4.0:

| | |
|---|---|
| Mannitol | 18.0 g |
| Sorbitol | 12.0 g |
| Gelatin G8-275 | 2.0 g |
| Gelatin Hydrolysate | 2.0 g |
| Citric Acid | 0.73 g |
| Ethanol | 300 ml |

The mixture was introduced into a Buchi model 190 spray drier with a heat setting of 8.8 which increased to 9.0 after the third time interval, an aspirator setting of 2 which changed to 3 after the second time interval, a flow rate setting of 5, a flow control setting of 700, and a vacuum setting of −20. Chamber temperatures were measured at approximately 5 minute consecutive intervals during the drying process. The temperatures at the flow inlet point were 61° C. (141° F.), 140° F., 58° C. (137° F.), 62° C. (144° F.), 62° C. (144° F.) and 63° C. (145° F.). The temperatures at the flow outlet point (the point where the dried product exits the drying chamber to product collector) were measured as 42° C. (107° F.), 34° C. (94° F.), 36° C. (96° F.), 36° C. (97° F.), 37° C. (99° F.), and 33° C. (92° F.). The particulate support matrix product had a bulk volume of about 275 ml, a specific bulk volume of about 21 ml/g and a porosity of 91.1%. Dissolution time was 1–5 seconds. A tablet produced from this matrix dissolved in about 3–5 seconds. When a quantity of an effervescent agent was added to the matrix prior to forming the tablet, the dissolution time was reduced to 15 seconds.

EXAMPLE 16

The following components were added to a quantity of purified water sufficient to produce a mixture with a volume of 1000 ml and a pH of 4.10.:

| | |
|---|---|
| Mannitol | 21.0 g |
| Sorbitol | 9.0 g |
| Gelatin G8-275 | 2.0 g |
| Gelatin Hydrolysate | 2.0 g |
| Citric Acid | 0.75 g |
| Sucrose | 1.5 g |
| Ethanol | 300 ml |

The mixture was introduced into a Buchi model 190 spray drier with a heat setting of 8.9, an aspirator setting of 2 which changed to 1 after the third time interval, a flow rate setting of 5, a flow control setting of 600, and a vacuum setting of −20 which changed to −15 after the second time interval. Chamber temperatures were measured at approximately 5 minute consecutive intervals during the drying process. The temperatures at the flow inlet point were 62° C. (143° F.), 62° C. (144° F.), 63° C. (145° F.), 63° C. (145° F.), 63° C. (145° F.) and 63° C. (145° F.). The temperatures at the flow outlet point (the point where the dried product exits the drying chamber to product collector) were measured as 36° C. (96° F.), 35° C. (95° F.), 34° C. (94° F.), 34° C. (94° F.), 34° C. (94° F.) and 34° C. (94° F.). The particulate support matrix product had a coarse texture and a bulk volume of about 200 ml, a specific bulk volume of about 20.5 ml/g and a porosity of 89.1%. Dissolution time was 2–3 seconds.

EXAMPLE 17

The following components were added to a quantity of purified water sufficient to produce a mixture with a volume of 1000 ml and a pH of 4.0:

|                    |         |
|--------------------|---------|
| Mannitol           | 21.0 g  |
| Sorbitol           | 9.0 g   |
| Gelatin G8-275     | 2.0 g   |
| Gelatin Hydrolysate| 2.0 g   |
| Citric Acid        | 0.76 g  |
| Explotab ®         | 0.6 g   |
| Ethanol            | 300 ml  |

The mixture was introduced into a Buchi model 190 spray drier with a heat setting of 8.9, an aspirator setting of 2 which was changed to 1 after the second time interval, a flow rate setting of 5, an initial flow control setting of 700 (changing to 650 after the second time interval), and a vacuum setting of −20. Chamber temperatures were measured at approximately 5 minute consecutive intervals during the drying process. The temperatures at the flow inlet point were 61° C. (141° F.), 63° C. (145° F.), 62° C. (143° F.), 62° C. (144° F.), 62° C. (144° F.) and 62° C. (144° F.). The temperatures at the flow outlet point (the point where the dried product exits the drying chamber to product collector) were measured as 33° C. (92° F.), 34° C. (93° F.), 33° C. (91° F.), 31° C. (87° F.), 31° C. (87° F.) and 31° C. (87° F.). The particulate support matrix product had a bulk volume of about 300 ml, a specific bulk volume of about 23 ml/g and a porosity of 89.8%. Dissolution time was about 2–3 seconds. A tablet formed from this mixture (except for Explotab®) had a dissolution time of from 1–5 seconds. When the tablet was coated with 0.5% PVP-10 in chloroform, dissolution time was 2–5 seconds.

EXAMPLE 18

The following components were added to a quantity of purified water sufficient to produce a mixture with a volume of 1000 ml and a pH of 4.2:

|                    |         |
|--------------------|---------|
| Mannitol           | 30.0 g  |
| Gelatin G8-275     | 2.0 g   |
| Gelatin Hydrolysate| 2.0 g   |
| Citric Acid        | 0.46 g  |
| Sucrose            | 0.56 g  |
| Explotab ®         | 0.6 g   |
| Ethanol            | 300 ml  |

The mixture was introduced into a Buchi model 190 spray drier with a heat setting of 8.9, an aspirator setting of 1, a flow rate setting of 5, a flow control setting of 650, and a vacuum setting of −15. Chamber temperatures were measured at approximately 5 minute consecutive intervals during the drying process. The temperatures at the flow inlet point were 67° C. (152° F.), 61° C. (142° F.), 63° C. (145° F.), and 63° C. (145° F.). The temperatures at the flow outlet point (the point where the dried product exits the drying chamber to product collector) were measured as 32° C. (90° F.), 27° C. (81° F.), 30° C. (86° F.), and 31° C. (87° F.). A particulate support matrix product having a rather small bulk volume of about 150 ml, a specific bulk volume of about 15 ml/g and a porosity of 85.5% was obtained. Dissolution time was about 5 seconds.

EXAMPLE 19

In a particularly preferred composition, the following components were added to a quantity of purified water sufficient to produce a mixture with a volume of 1000 ml and a pH of 4.2:

|                      |         |
|----------------------|---------|
| Gelatin G8-275       | 1.0 g   |
| Gelatin Hydrolysate  | 3.0 g   |
| Mannitol             | 20.0 g  |
| Xylitol              | 5.0 g   |
| Sorbitol             | 5.0 g   |
| Sucrose              | .68 g   |
| Citric Acid          | 1.0 g   |
| Propylene glycol     | 10 drops|
| Acetic Acid, glacial | 6 drops |
| Ethanol              | 300 ml  |

After spray drying this product produces approximately 300 mL. To produce a tablet, the above powder may be placed in the cavity of a standard tabletting machine and the pressure adjusted to yield a tablet which can remain intact for handling but retains its light weight.

Coating Solutions

The following are examples of coating compositions which can be used to coat the formed tablets. Coating agents can be applied by dropping, by spraying or by passing the tablet through an environment saturated with the coating agent.

|       |                  |                  |
|-------|------------------|------------------|
| I.    | PVP-40           | 10%              |
|       | PEG 1450         | 10%              |
|       | Chloroform       | 80%              |
| II.   | PVP-10           | 100 mg           |
|       | Absolute Alcohol | 5 ml             |
|       | Ether            | 18 ml            |
| III.  | PEG 1450         | 170 mg           |
|       | Absolute Alcohol | 7 ml             |
|       | Ether            | 14 ml            |
| IV.   | PVP-10           | 0.5%             |
|       | PVP-40           | 0.5%             |
|       | PEG 1540         | 1.0%             |
|       | Chloroform       | 98%              |
| V.    | PVP-10           | 1.0%             |
|       | PVP-40           | 1.0%             |
|       | PEG 1450         | 1%               |
|       | PEG 3350         | 1%               |
|       | Chloroform       | 96%              |
| VI.   | PEG 1450         | 5%               |
|       | PEG 3350         | 5%               |
|       | Chloroform       | 90%              |
| VII.  | PEG 1450         | 5%               |
|       | PEG 3350         | 5%               |
|       | PVP 10/PVP40     | 0.1–0.5%         |
|       |                  | (one or the other)|
|       | Chloroform       | 89.5%            |
| VIII. | PEG 3350         | 20.g             |
|       | Acetone to make  | 100 ml           |

Acetone may be substituted for chloroform or ether in the above formulations. Formulas VI and VIII are preferred coating compositions due to their tendency to leave tablet volume unaffected. Solvents other than ether, alcohol and chloroform may be used. These include ethyl acetate and other types of organic solvents.

Changes may be made in the construction and the operation of the various components, elements and assemblies described herein or in the steps or the sequence of steps of the methods described herein without departing from the spirit and scope of the invention as defined in the following claims.

What is claimed is:

1. A rapidly dissolving solid pharmaceutical dosage form, comprising:
   a particulate support matrix comprising an effective amount of a first polypeptide component having a predetermined net charge, an effective amount of a second polypeptide component having a predetermined net charge of the same sign as the net charge of the first polypeptide component, and a bulking agent, and wherein the first polypeptide component and the second polypeptide component together comprise about 2% to 20% by weight of the particulate support matrix and wherein the bulking agent comprises about 60% to 96% by weight of the particulate support matrix, and wherein the second polypeptide component has a solubility in aqueous solution greater than that of the first polypeptide component; and a pharmaceutical ingredient dispersed throughout the particulate support matrix; and wherein when the dosage form is introduced into an aqueous environment the support matrix is substantially completely disintegrable within less than about 20 seconds.

2. The particulate support matrix of claim 1 wherein the first polypeptide component comprises a non-hydrolyzed gelatin and the second polypeptide component comprises a hydrolyzed gelatin.

3. The particulate support matrix of claim 1 wherein the first polypeptide component and the second polypeptide component both have a net positive charge.

4. The particulate support matrix of claim 2 wherein the nonhydrolyzed gelatin and the hydrolyzed gelatin both have a net positive charge.

5. The particulate support matrix of claim 1 wherein the first polypeptide component and the second polypeptide component both have a net negative charge.

6. The dosage form of claim 1 further comprising up to 5% of an effervescing agent.

7. The dosage form of claim 1 further comprising binding agent.

8. The dosage form of claim 1 further comprising a flavoring agent.

9. The dosage form of claim 1 further comprising a polymeric coating on the external surface of the dosage form.

10. The dosage form of claim 1 wherein the density of the dosage form is within a range of about 0.1 ml to about 0.2 g/ml.

11. A rapidly dissolving solid pharmaceutical dosage form, comprising:

a particulate support matrix comprising an effective amount of a first gelatin component having a predetermined net charge, an effective amount of a second gelatin component having a predetermined net charge of the same sign as the net charge of the first gelatin component, and a bulking agent, and wherein the first gelatin component and the second gelatin component together comprise about 2% to 20% by weight of the particulate support matrix and wherein the bulking agent comprises about 60% to 96% by weight of the particulate support matrix, and wherein the second gelatin component has a solubility in aqueous solution greater than that of the first gelatin component; and a pharmaceutical ingredient dispersed throughout the particulate support matrix; and wherein when the dosage form is introduced into an aqueous environment the support matrix is substantially completely disintegrable within less than about 20 seconds.

12. The particulate support matrix of claim 1 wherein the first gelatin component comprises a non-hydrolyzed gelatin and the second gelatin component comprises a hydrolyzed gelatin.

13. The particulate support matrix of claim 1 wherein the first gelatin component and the second gelatin component both have a net positive charge.

14. The dosage form of claim 11 further comprising an effervescing agent.

15. The dosage form of claim 11 further comprising a binding agent.

16. The dosage form of claim 11 further comprising a flavoring agent.

17. The dosage form of claim 11 further comprising a polymeric coating on the external surface of the dosage form.

18. The dosage form of claim 11 wherein the density of the dosage form is within a range of about 0.1 g/ml to about 0.2 g/ml.

19. A rapidly dissolving solid pharmaceutical dosage form produced by the process comprising:

providing a predetermined quantity of a particulate support matrix produced by the process of providing an aqueous composition comprising:

an aqueous medium, a support agent comprising an effective amount of polymeric primary component having a predetermined net charge, an effective amount of a solubilizing component comprising a polymer or hydrolyzed polymer having a predetermined net charge of the same sign as the primary component, and a bulking agent and wherein the polymeric primary component and the solubilizing component together comprise about 2% to 20% by weight of the particulate support matrix and wherein the bulking agent comprises about 60% to 96% by weight of the particulate support matrix, and wherein the solubilizing component has a solubility in aqueous solution greater than that of the polymeric primary component, and a volatilizing agent for enhancing the rate of vaporization of the aqueous medium; and introducing the aqueous composition as droplets into a drying chamber heated to a predetermined temperature causing evaporation of the aqueous medium and volatilizing agent from the droplets leaving the support agent in a dried particulate form comprising the particulate support matrix;

providing a pharmaceutical ingredient;

combining the predetermined quantity of the particulate support matrix with a predetermined quantity of the pharmaceutical ingredient and dispersing the pharmaceutical ingredient throughout the support matrix to form a dosage mixture; and forming the dosage mixture into a dosage form which when introduced into an aqueous environment is substantially completely disintegrable within less than about 20 seconds.

20. The dosage form of claim 19 wherein in the step of introducing the aqueous composition, the particulate support matrix produced thereby further comprises a density within a range of about 0.03 g/ml to about 0.06 g/ml.

21. The dosage form of claim 19 wherein in the step of providing the aqueous composition the polymeric primary component comprises a first polypeptide and the solubilizing component of the support matrix comprises a second polypeptide.

22. The dosage form of claim 21 wherein the first polypeptide comprises a non-hydrolyzed gelatin and the second polypeptide comprises a hydrolyzed gelatin.

23. The dosage form of claim 21 wherein the first polypeptide and the second polypeptide both have a net positive charge.

24. The dosage form of claim 22 wherein the non-hydrolyzed gelatin and the hydrolyzed gelatin both have a net positive charge.

25. The dosage form of claim 21 wherein the first polypeptide and the second polypeptide both have a net negative charge.

26. The dosage form of claim 19 further comprising a coating applied to the external surface of the dosage form.

27. The dosage form of claim 19 further comprising an effervescing agent added to the particulate support matrix.

28. The dosage form of claim 19 further comprising a binding agent added to the particulate support matrix.

29. The dosage form of claim 19 further comprising a flavoring agent added to the particulate support matrix.

30. The dosage form of claim 19 wherein the support matrix is substantially completely disintegrable within less than about 10 seconds when the dosage form is introduced into an aqueous environment.

31. The dosage form of claim 19 wherein the support matrix is substantially completely disintegrable within from about 1 second to about 6 seconds when the dosage form is introduced into an aqueous environment.

* * * * *

UNITED STATES PATENT AND TRADEMARK OFFICE
CERTIFICATE OF CORRECTION

PATENT NO. : 5,776,491
DATED : July 7, 1998
INVENTOR(S) : Loyd V. Allen, Jr. et al.

Page 1 of 5

It is certified that error appears in the above-identified patent and that said Letters Patent is hereby corrected as shown below:

THE COVER PAGE:

In the "[*] Notice:" regarding the terminal disclaimer, delete "Pat. No. 5,766,630" and substitute therefor -- Pat. No. 5,595,761--

IN THE DESCRIPTION:

Col. 5: line 37, delete "comprises" and substitute --comprises,-- therefor.

line 38, delete "version" and substitute --version,-- therefor.

Col. 6: line 19, after "including" insert --proteins--.

Col. 7: line 21, delete "result of" and substitute --results in--.

line 23, delete "solvent" and substitute --solvent,-- therefor.

line 36, delete "solution" and substitute --solution,-- therefor.

line 41, delete "agent" and substitute --agent,-- therefor.

line 42, delete "bonate" and substitute --bonate,-- therefor.

Col. 10: lines 64 and 65, delete "69° C. (156° F.), 69° C. (156° F.), 71° C. (159° F.), 68° C. (154° F.), and 69° C. (157° F.)", and substitute therefor --156° C., 156° C., 159° C., 154° C., and 157° C.--.

Col. 10: line 67 to
Col. 11: line 2, delete "46° C. (115° F.), 44° C. (111° F.), 30° C. (86° F.), 43° C. (109° F.), and 42° C. (108° F.)", and substitute therefor --115° C., 111° C., 86° C., 109° C., and 108° C.--.

Col. 11: lines 26 and 27, delete "68° C. (154° F.), 68° C. (154° F.), 56° C (133° F.), 62° C. (143° F.), and 62° C. (143° F.)" and substitute therefor --154° C., 154° C., 133° C., 143° C., and 143° C.--.

lines 30 and 31, delete "40° C. (104° F.), 40° C. (104° F.), 32° C. (90° F.), 34° C. (93° F.), 34° C. (93° F.), and 34° C. (93° F.)" and substitute therefor --104° C., 104° C., 90° C., 93° C., 93° C., and 93° C.--.

UNITED STATES PATENT AND TRADEMARK OFFICE
CERTIFICATE OF CORRECTION

PATENT NO.     :  5,776,491

DATED          :  July 7, 1998

INVENTOR(S)    :  Loyd V. Allen, Jr. et al.

It is certified that error appears in the above-identified patent and that said Letters Patent is hereby corrected as shown below:

Col. 11:  lines 59 and 60, delete "68° C. (154° F.), 69° C. (157° F.), 69° C. (157° F.), 69° C. (157° F.), and 69° C. (157° F.)" and substitute therefor --154° C., 157° C., 157° C., 157° C., and 157° C.--.

lines 62-64, delete "42° C. (107° F.), 42° C. (108° F.), 42° C. (108° F.), 42° C. (108° F.), and 42° C. (108° F.)" and substitute therefor --107° C., 108° C., 108° C., 108° C., and 108° C.--.

Col. 12:  lines 25 and 26, delete "68° C. (155° F.), 66° C. (150° F.), and 68° C. (155° F.)" and substitute therefor --155° C., 150° C., and 155° C.--.

lines 28 and 29, delete "46° C. (114° F.), 43° C. (109° F.) and 42° C. (108° F.)" and substitute therefor --114° C., 109° C. and 108° C.--.

Col. 13:  line 5, delete "°C.  49  72  90  87  104  102  107  108".

line 6, delete "°F." and substitute therefor --°C.--.

line 8, delete "°C.  36  37  37  37  39  40  41  41".

line 9, delete "°F." and substitute therefor --°C.--.

line 48, delete "°C.  33  34  38  66  66  79".

line 49, delete "°F." and substitute therefor --°C.--.

line 52, delete "°C.  22  24  28  47  48  42".

line 53, delete "°F." and substitute therefor --°C.--.

Col. 14:  lines 14 and 15, delete "69° C. (156° F.), 69° C. (156° F.), 69° C. (156° F.), 69° C. (156° F.), and 68° C. (155° F.)" and substitute therefor --156° C., 156° C., 156° C., 156° C., and 155° C.--.

lines 17-19, delete "46° C. (114° F.), 42° C. (108° F.), 33° C. (92° F.), 32° C. (89° F.), and 29° C. (84° F.)" and substitute therefor --114° C., 108° C., 92° C., 89° C., and 84° C.--.

lines 46-47, delete "71° C. (160° F.), 69° C. (157° F.), 69° C. (157° F.), 69° C. (156° F.), and 68° C. (155° F.)" and substitute therefor --160° C., 157° C., 157° C., 156° C., and 155° C.--.

UNITED STATES PATENT AND TRADEMARK OFFICE
CERTIFICATE OF CORRECTION

PATENT NO. : 5,776,491

DATED : July 7, 1998

INVENTOR(S) : Loyd V. Allen, Jr. et al.

It is certified that error appears in the above-identified patent and that said Letters Patent is hereby corrected as shown below:

Col. 14: lines 49-51, delete "46° C. (115° F.), 42° C. (108° F.), 42° C. (107° F.), 42° C. (108° F.), and 42° C. (108° F.)" and substitute therefor --115° C., 108° C., 107° C., 108° C., and 108° C.--.

Col. 15: lines 13-14, delete "69° C. (156° F.), 68° C. (155° F.), 69° C. (156° F.), 68° C. (155° F.), and 68° C. (155° F.)" and substitute therefor --156° C., 155° C., 156° C., 155° C., and 155° C.--.

lines 16-18, delete "47° C. (117° F.), 45° C. (113° F.), 41° C. (106° F.), 42° C. (108° F.), and 42° C. (107° F.)" and substitute therefor --117° C., 113° C., 106° C., 108° C., and 107° C.--.

lines 46-47, delete "59° C. (139° F.), 62° C. (143° F.), 62° C. (144° F.), 62° C. (144° F.), and 61° C. (142° F.)" and substitute therefor --139° C., 143° C., 144° C., 144° C., and 142° C.--.

lines 50-51, delete "39° C. (102° F.), 34° C. (94° F.), 36° C. (97° F.), 40° C. (104° F.), and 34° C. (94° F.)" and substitute therefor --102° C., 94° C., 97° C., 104° C., and 94° C.--.

Col. 16: lines 15-16, delete "64° C. (148° F.), 64° C. (147° F.), 64° C. (147° F.), 64° C. (147° F.), and 64° C. (147° F.)" and substitute therefor --148° C., 147° C., 147° C., 147° C., and 147° C.--.

lines 18-20, delete "47° C. (116° F.), 41° C. (105° F.), 39° C. (103° F.), 39° C. (102° F.), and 39° C. (102° F.)" and substitute therefor --116° C., 105° C., 103° C., 102° C., and 102° C.--.

lines 46-47, delete "68° C. (154° F.), 64° C. (148° F.), 63° C. (145° F.), 63° C. (145° F.), 63° C. (145° F.) and 64° C. (147° F.)" and substitute therefor --154° C., 148° C., 145° C., 145° C., 145° C., and 147° C.--.

lines 50-52, delete "40° C. (104° F.), 40° C. (104° F.), 37° C. (98° F.), 35° C. (95° F.), 35° C. (95° F.) and 37° C. (98° F.)" and substitute therefor --104° C., 104° C., 98° C., 95° C., 95° C., and 98° C.--.

Col. 17: lines 15-17, delete "55° C. (131° F.), 55° C. (131° F.), 55° C. (131° F.), 55° C. (131° F.), 55° C. (131° F.) and 55° C. (131° F.)" and substitute therefor --131° C., 131° C., 131° C., 131° C., 131° C., and 131° C.--.

UNITED STATES PATENT AND TRADEMARK OFFICE
CERTIFICATE OF CORRECTION

PATENT NO.   : 5,776,491
DATED        : July 7, 1998
INVENTOR(S)  : Loyd V. Allen, Jr. et al.

Page 4 of 5

It is certified that error appears in the above-identified patent and that said Letters Patent is hereby corrected as shown below:

Col. 17:   lines 19-21, delete "34° C. (94° F.), 34° C. (94° F.), 34° C. (94° F.), 35° C. (95° F.), 35° C. (95° F.) and 35° C. (95° F.)" and substitute therefor --94° C., 94° C., 94° C., 95° C., 95° C., and 95° C.--.

lines 49-51, delete "59° C. (139° F.), 55° C. (131° F.), 61° C. (141° F.), 59° C. (138° F.), 58° C. (137° F.), 136° F. and 58° C. (137° F.)" and substitute therefor --139° C., 131° C., 141° C., 138° C., 137° C., 136° C., and 137° C.--.

lines 54-55, delete "36° C. (96° F.), 32° C. (89° F.), 34° C. (93° F.), 33° C. (92° F.), 34° C. (93° F.), 34° C. (93° F.) and 34° C. (93° F.)" and substitute therefor --96° C., 89° C., 93° C., 92° C., 93° C., 93° C., and 93° C.--.

Col. 18:   lines 17-18, delete "61° C. (141° F.), 140° F., 58° C. (137° F.), 62° C. (144° F.), 62° C. (144° F.) and 63° C. (145° F.)" and substitute therefor --141° C., 140° C., 137° C., 144° C., 144° C., and 145° C.--.

lines 20-22, delete "42° C. (107° F.), 34° C. (94° F.), 36° C. (96° F.), 36° C. (97° F.), 37° C. (99° F.), and 33° C. (92° F.)" and substitute therefor --107° C., 94° C., 96° C., 97° C., 99° C., and 92° C.--.

line 28, delete "15" and substitute --1-5-- therefor.

lines 52-54, delete "62° C. (143° F.), 62° C. (144° F.), 63° C. (145° F.), 63° C. (145° F.), 63° C. (145° F.), and 63° C. (145° F.)" and substitute therefor --143° C., 144° C., 145° C., 145° C., 145° C., and 145° C.--.

lines 56-58, delete "36° C. (96° F.), 35° C. (95° F.), 34° C. (94° F.), 34° C. (94° F.), 34° C. (94° F.) and 34° C. (94° F.)" and substitute therefor --96° C., 95° C., 94° C., 94° C., 94° C., and 94° C.--.

Col. 19:   lines 18-19, delete "61° C. (141° F.), 63° C. (145° F.), 62° C. (143° F.), 62° C. (144° F.), 62° C. (144° F.) and 62° C. (144° F.)" and substitute therefor --141° C., 145° C., 143° C., 144° C., 144° C., and 144° C.--.

lines 22-24, delete "33° C. (92° F.), 34° C. (93° F.), 33° C. (91° F.), 31° C. (87° F.), 31° C. (87° F.) and 31° C. (87° F.)" and substitute therefor --92° C., 93° C., 91° C., 87° C., 87° C., and 87° C.--.

UNITED STATES PATENT AND TRADEMARK OFFICE
CERTIFICATE OF CORRECTION

PATENT NO. : 5,776,491
DATED : July 7, 1998
INVENTOR(S) : Loyd V. Allen, Jr. et al.

It is certified that error appears in the above-identified patent and that said Letters Patent is hereby corrected as shown below:

Col. 19: lines 52-53, delete "67° C. (152° F.), 61° C. (142° F.), 63° C. (145° F.), and 63° C. (145° F.)" and substitute therefor --152° C., 142° C., 145° C., and 145° C.--.

lines 55-56, delete "32° C. (90° F.), 27° C. (81° F.), 30° C. (86° F.), and 31° C. (87° F.)" and substitute therefor --90° C., 81° C., 86° C., and 87° C.--.

Col. 21: line 25 (claim 4, line 2), delete "nonhydrolyzed" and substitute --non-hydrolyzed-- therefor.

line 64 (claim 12, line 1), delete "1" and substitute --11-- therefor.

Col. 22: line 1 (claim 13, line 1), delete "1" and substitute --11-- therefor.

Signed and Sealed this

Fourteenth Day of September, 1999

Attest:

Q. TODD DICKINSON

*Attesting Officer*  *Acting Commissioner of Patents and Trademarks*